United States Patent
Yang et al.

(10) Patent No.: US 9,650,326 B2
(45) Date of Patent: May 16, 2017

(54) PROCESS FOR TREATING REACTION SOLUTION CONTAINING LONG CHAIN DICARBOXYLATE

(75) Inventors: Xiwei Yang, Shanghai (CN); Chi Liu, Shanghai (CN); Bingbing Qin, Shanghai (CN); Yi Zheng, Shanghai (CN); Naiqiang Li, Shanghai (CN)

(73) Assignees: Cathay R&D Center Co., Ltd., Shanghai (CN); Cathay Industrial Biotech Ltd., Grand Cayman (KY)

( * ) Notice: Subject to any disclaimer, the term of this patent is extended or adjusted under 35 U.S.C. 154(b) by 0 days.

(21) Appl. No.: 14/376,784

(22) PCT Filed: Mar. 12, 2012

(86) PCT No.: PCT/CN2012/072178
§ 371 (c)(1),
(2), (4) Date: Aug. 5, 2014

(87) PCT Pub. No.: WO2013/117026
PCT Pub. Date: Aug. 15, 2013

(65) Prior Publication Data
US 2015/0025259 A1    Jan. 22, 2015

(30) Foreign Application Priority Data
Feb. 8, 2012  (CN) .......................... 2012 1 0027749

(51) Int. Cl.
*C07C 51/09* (2006.01)
*C07C 51/02* (2006.01)
*C07C 51/48* (2006.01)

(52) U.S. Cl.
CPC ............. *C07C 51/09* (2013.01); *C07C 51/02* (2013.01); *C07C 51/48* (2013.01)

(58) Field of Classification Search
None
See application file for complete search history.

(56) References Cited

U.S. PATENT DOCUMENTS

| | | | |
|---|---|---|---|
| 5,254,466 A * | 10/1993 | Picataggio | C12N 15/00 435/142 |
| 5,753,704 A | 5/1998 | Lindner et al. | |
| 6,660,505 B2 * | 12/2003 | Staley | C07C 51/48 435/136 |
| 6,777,213 B2 * | 8/2004 | Staley | C07C 51/36 435/134 |
| 2009/0054610 A1 | 2/2009 | Gross et al. | |
| 2009/0305367 A1 * | 12/2009 | Kamal et al. | 435/142 |

FOREIGN PATENT DOCUMENTS

CN    1570124 A    1/2005

OTHER PUBLICATIONS

Zuo, H. et al., Study on processing technology of recovering tridecane dicarboxlic acid (DCA 13) Filtrate, 2005, Jiangxi Chemical, issue 4, pp. 139-141 (English translation).*
International Search Report (English translation) corresponding to PCT/CN2012/072178 mailed Nov. 22, 2012, 3 pages.
Zuo, Feihong et al. (Non-English; CN version), "Study on Processing Technology of Recover Tridecane Dicarboxylic Acid from Mother Liquor," *Jiangxi Chemical Industry* (2005) 4:139-141.

* cited by examiner

*Primary Examiner* — Yate K Cutliff
(74) *Attorney, Agent, or Firm* — Kilpatrick Townsend and Stockton LLP

(57) ABSTRACT

Disclosed is a process for treating a reaction solution containing a long chain dicarboxylate. The process is characterized by comprising: acidifying a reaction solution so as to convert the long chain dicarboxylate into a long chain dicarboxylic acid, adding an extractant so as to extract the resulting long chain dicarboxylic acid, separating the phase rich in the long chain dicarboxylic acid, and further separating the long chain dicarboxylic acid. The process of the present invention has the following advantages: 1) the processing route is simple, the operation time is short, less equipment is required, and the production efficiency is high; 2) product yield is high; 3) product quality is good, purity in the resulting products is high, and the color is lighter; and 4) no active carbon is consumed and the solvent can be recycled, thereby saving resources and being environmentally friendly.

13 Claims, No Drawings

PROCESS FOR TREATING REACTION SOLUTION CONTAINING LONG CHAIN DICARBOXYLATE

TECHNICAL FIELD

The present invention relates to a process for treating a reaction solution. More specifically, the present invention is directed to a process for treating a reaction solution containing a long chain dicarboxylate.

BACKGROUND OF THE INVENTION

Long chain dicarboxylic acids are basic monomer raw materials of a series of synthetic materials. Long chain dicarboxylic acids and derivative monomers thereof can be used for producing nylon, polycarbonate, powder coatings, perfumes, hot melt adhesives and special lubricants and the like, and are important raw materials for such products as synthetic perfumes, engineering plastics, cold resistant plasticizers, high grade lubricants and polyamide hot melt adhesives.

During the preparation of a long chain dicarboxylic acid, a long chain dicarboxylate is firstly formed in a reaction solution generally, and the reaction solution containing the long chain dicarboxylate needs to be subjected to a series of treatments, so as to obtain a long chain dicarboxylic acid product.

During a biological fermentation process for producing a long chain dicarboxylic acid, a fermentation broth after the fermentation is ended contains a long chain dicarboxylate, and further contains microbial cells and other impurities, such as residual alkanes or fatty acids. The fermentation broth needs to be treated, so as to obtain the long chain dicarboxylic acid.

Presently, a process for obtaining a long chain dicarboxylic acid from a fermentation broth includes performing pretreatments such as microbial cells removal, decolorization, acidification, filtration and the like firstly to obtain a primary product, and then performing treatments such as recrystallization, decolorization, washing and the like. The steps of this process are too long, and the production costs are high.

Chinese Patent Application No. 200410018255.7 teaches a process for producing a normal long chain dicarboxylic acid, wherein a fermentation broth is subjected to a series of treatments of microbial cells removal by a ceramic membrane, decolorization by active carbon, acidification by an inorganic acid, plate-and-frame filtration and the like, so as to obtain a dicarboxylic acid product. The treatment process has the following disadvantages: 1) the process route is complex, the operation cycle is long, more equipment is required, and the production efficiency is low; 2) the product yield is low and generally is 93% to 95% only; 3) the product quality is poor, the salt content of the resulting dicarboxylic acid product is high, and the color is dark; 4) a large amount of active carbon is needed to be consumed, and the amount of the active carbon used is up to 5% to 10% based on the amount of the product, which causes waste of resources and environmental pollution because the active carbon after the decolorization cannot be recycled. The dicarboxylic acid product obtained through this process needs to be subjected to further refining treatments, so as to meet the requirements of most customers for the quality of the long chain dicarboxylic acid.

A novel process for directly treating a reaction solution to obtain a long chain dicarboxylic acid product at a high yield has been always desired.

SUMMARY OF THE INVENTION

A technical problem to be solved by the present invention is to provide a process for treating a reaction solution containing a long chain dicarboxylate to obtain a long chain dicarboxylic acid product at a high yield.

The technical problem to be solved by the present invention is solved by the following implementation solutions:

A process for treating a reaction solution containing a long chain dicarboxylate, which is characterized by comprising: acidifying the reaction solution so as to convert the long chain dicarboxylate into a long chain dicarboxylic acid, adding an extractant so as to extract the resulting long chain dicarboxylic acid, separating the phase rich in the long chain dicarboxylic acid, and further separating out the long chain dicarboxylic acid, wherein the extraction is performed at a temperature in a range from room temperature to the boiling point of the phase rich in the long chain dicarboxylic acid and below 100° C.

The reaction solution in the present invention is a mixture obtained after the reaction with water as the reaction medium.

The reaction solution is a fermentation broth or a treated fermentation broth wherein the treated fermentation broth is a solution obtained after removing or reducing the content of one or more other components other than the long chain dicarboxylate in the fermentation broth.

The fermentation broth contains the long chain dicarboxylate, microbial cells and other impurities.

The fermentation broth treated can be obtained by removing or reducing the content of one or more other components other than the long chain dicarboxylate in the fermentation broth by means of filtration through a ceramic membrane, a centrifuge, flocculation filtration, active carbon filtration, and the like.

The long chain dicarboxylic acid can be further separated by cooling the phase rich in the long chain dicarboxylic acid and separating the precipitated long chain dicarboxylic acid or by heating the phase rich in the long chain dicarboxylic acid to evaporate the extractant.

The long chain dicarboxylic acid may be a saturated or unsaturated straight chain dicarboxylic acid having 9 to 18 carbon atoms, with carboxyl group at two ends of the chain.

The long chain dicarboxylic acid may be selected from: nonanedioic acid, decanedioic acid, undecanedioic acid, dodecanedioic acid, tridecanedioic acid, tetradecanedioic acid, pentadecanedioic acid, hexadecanedioic acid, heptadecanedioic acid, octadecanedioic acid and 9-ene-octadecanedioic acid.

The extractant may be selected from $C_2$-$C_8$ alcohol esters of formic acid or acetic acid, $C_4$-$C_8$ alcohols, ketones, benzenes and alkenes or a mixture of two or more thereof.

The extractant includes, but not limited to, n-butanol, isobutanol, n-pentanol, isopentanol, hexanol, cyclohexanol, 2-ethylhexanol, isooctanol, sec-octanol, toluene, xylene, ethylbenzene, chloroform, perchloroethylene, methyl isobutyl ketone (MIBK), butyl formate, propyl acetate, isoamyl acetate, isobutyl acetate, isopropyl acetate, n-amyl acetate, ethyl acetate, butyl acetate, octyl acetate, isooctyl acetate, sec-octyl acetate, isopropyl ether, butyl ether, amyl ether, isoamyl or a mixture of two or more thereof.

In an embodiment, the extractant is a mixture of butyl acetate and n-butanol.

The acidification step is generally performed by using an inorganic acid, such as hydrochloric acid, sulfuric acid, phosphoric acid and nitric acid, preferably sulfuric acid.

The amount of the extractant is greater than the effective amount for dissolving the long chain dicarboxylic acid.

Preferably, the extraction is performed at a temperature in the range from 60° C. to the boiling point of the phase rich in the long chain dicarboxylic acid and below 100° C.

In some embodiments, the extraction is performed at above 75° C. In some embodiments, the extraction is performed at above 80° C. In some embodiments, the extraction is performed at above 85° C. In some embodiments, the extraction is performed at above 90° C. In some embodiments, the extraction is performed at above 95° C.

The aim of acidification is to completely convert the dicarboxylate in the reaction solution into a dicarboxylic acid, so as to ensure that the extraction can be performed smoothly.

It should be understood by persons skilled in the art that the step of adding the acid and the step of adding the extractant in the present invention may be performed in any sequences or at the same time.

It should be noted that, the term "the boiling point of the phase rich in the long chain dicarboxylic acid" as used in the present invention refers to the boiling point of the extractant in the case that the extractant and water have no azeotropic point, and refers to the azeotropic point of the extractant and water in the case that the extractant and water have an azeotropic point.

The term "effective amount for dissolving the long chain dicarboxylic acid" as used in the present invention refers to the amount of a solvent for effectively dissolving the resulting long chain dicarboxylic acid in the reaction solution after acidification.

Persons skilled in the art can easily determine the effective amount for dissolving the long chain dicarboxylic acid by detecting the content of the long chain dicarboxylate in the reaction solution.

The inventors of the present invention unexpectedly found that, the product obtained through direct acidification and extraction without removing the microbial cells and residual alkanes or fatty acids in the fermentation broth is superior in term of purity, color and the like to that obtained through filtration, decolorization, and then acidification and filtration at a decreased temperature. The reason may lies in that, under the extraction condition, the solubility of pigment impurities in the fermentation broth is not high in the organic phase, so that not only the dicarboxylic acid can be extracted efficiently during the extraction, but also the pigment can be effectively removed. By means of this finding, waste of resources and costs caused by use of a large amount of active carbon for decolorization in the prior art can be avoided, and at the same time, the yield of the dicarboxylic acid is improved.

The extraction temperature and time are slightly different due to different extractants and dicarboxylic acids. Generally, it is needed to add sufficient extractant and heat the solution to a suitable extraction temperature, so as to ensure that the dicarboxylic acid can be totally dissolved in the organic phase. When extracting at a higher temperature, the high solubility of the product in the extractant is beneficial to full utilization of the extractant, thereby reducing the amount of the extractant used. The extraction time is preferably one that ensures full contact of the organic phase and water phase for full extraction, and under a common stirring condition, the extraction time is not less than 5 minutes.

The inventors of the present invention found through tests that, when the extraction is performed at the extraction temperature used in the present invention, good layering of the water phase and the organic phase is achieved.

Compared with the processes for treating a reaction solution containing a long chain dicarboxylic acid in the prior art, the process of the present invention has the following advantages: 1) the process route is short, the operation cycle is short, less equipment is required, and the production efficiency is high; 2) the product yield is high; 3) the product quality is good, the purity in the resulting products is high, and the color is lighter; and 4) no active carbon is needed to be consumed and the solvent can be recycled, thereby saving resources and being environmentally friendly.

DETAILED DESCRIPTION OF THE PREFERRED EMBODIMENTS

The present invention is described below in detail through examples, to make the features and advantages of the present invention clearer, but the present invention is not limited to the examples listed herein.

In the examples listed herein, the following test methods are used:

1. Detection of dicarboxylic acid by gas chromatography:

A standard dicarboxylic acid sample is used as a control, and the determination of fatty acids in baby's foods and milk products in GB5413.27-2010 is for reference.

2. Ash content detection:

A sample to be tested is burnt in a crucible, then burnt in a Muffle furnace for 2 hours at 700° C. to 800° C., and weighed after cooling to a constant weight, and the weight percent is calculated.

3. Determination of total nitrogen:

The determination is performed by adopting the Kjeldahl method.

4. Determination of transmittance:

A dicarboxylic acid sample is dissolved in a 5% sodium salt aqueous solution, and then the transmittance at 430 nm is detected via UV.

The processes for preparing the fermentation broth, the clear solution from the fermentation broth after passing through a ceramic membrane, the clear solution of the fermentation broth after centrifugation that are used in the following comparative example and the examples can be seen in Patent ZL200410018255.7.

Comparative Example 1

100 L of a dodecanedioic acid fermentation broth after the termination of fermentation in Example 4 of Patent ZL200410018255.7 was taken, in which the dicarboxylic acid content was 168 g/L, and heated to 70° C. by a vapor heat exchanger, then an alkali was added to adjust the pH value to 8.5, and microbial cells were removed by filtering through a ceramic membrane, to obtain a dodecanedioic acid membrane-filtered clear solution. To the membrane-filtered clear solution, powder active carbon was added at an amount of 6% based on the total weight of the dicarboxylic acid in the solution, and the solution was stirred for 1 hour and filtered, to obtain a dodecanedioic acid decolorized solution. To the decolored solution, sulfuric acid was added to adjust the pH value to 3, and then the solution was filtered, to obtain the dodecanedioic acid product, with the product yield being 94%. The resulting product was detected for the dicarboxylic acid content, the ash content, the nitrogen content and the transmittance, with the results seen in Table 1.

Example 1

About 2,000 ml (2,120 g) of a tridecanedioic acid fermentation broth after the termination of fermentation according to the method described in Example 5 of Patent ZL200410018255.7 was taken, in which the dicarboxylic acid content was 165 g/L. 1,800 g MIBK was added to the tridecanedioic acid fermentation broth, and then about 270 ml of 50% sulfuric acid was added for acidification. The solution was maintained in a water bath at 90° C. to 95° C. and stirred for 1 hour, and then separated by using a separatory funnel. The dicarboxylic acid content in the wastewater obtained through the separation was lower than 0.2%, and the extraction yield of the organic phase was greater than 98%. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 2

1,800 ml of an undecanedioic acid fermentation broth after the termination of fermentation according to the method described in Example 3 of Patent ZL200410018255.7 was taken, in which the dicarboxylic acid content was 120 g/L. About 1,800 g of toluene was added to the undecanedioic acid fermentation broth, and then about 300 ml of 35% hydrochloric acid was added for acidification. The solution was maintained in a water bath at 80° C. to 83° C. and stirred for 10 hours, and then separated by using a separatory funnel. The organic phase obtained through the separation was cooled to room temperature and filtered, to obtain the dicarboxylic acid product. The extraction yield of the dicarboxylic acid was detected to be greater than 97%. The resulting product was detected for the dicarboxylic acid content, the ash content, the nitrogen content and the transmittance, with the results seen in Table 1.

Example 3

600 ml of a tetradecanedioic acid membrane-filtered clear solution with microbial cells removed by a ceramic membrane after the termination of fermentation according to the method described in Example 6 of Patent ZL200410018255.7 was taken, in which the dicarboxylic acid content was 10%. To the tetradecanedioic acid membrane clear solution, 35 ml of 98% concentrated sulfuric acid was added, and then about 400 g of n-butanol was added. The solution was maintained in a water bath at 85° C. and stirred for 10 minutes, and then separated by using a separatory funnel. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 4

700 ml of a dodecanedioic acid fermentation broth after the termination of fermentation according to the method described in Example 4 of Patent ZL200410018255.7 was taken and centrifuged to remove microbial cells, and 600 ml clear solution was obtained, in which the dicarboxylic acid content was 168 g/L. To the dodecanedioic acid solution with microbial cells removed, 43 ml of 98% concentrated sulfuric acid was added, and then about 700 g of butyl acetate was added. The solution was maintained in a water bath at 85° C. and stirred for 1 hour, and then separated by using a separatory funnel. The dicarboxylic acid content in the wastewater obtained through the separation was lower than 0.2%, and the extraction yield of the organic phase was greater than 98%. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 5

600 ml of a 9-ene-octadecanedioic acid fermentation broth after the termination of fermentation according to the method described in Example 2 of Patent ZL200410018255.7 was taken, in which the dicarboxylic acid content was 7.75%. To the 9-ene-octadecanedioic acid fermentation broth, 20 ml of 98% concentrated sulfuric acid was added, and then about 700 g of ethyl acetate was added. The solution was maintained in a water bath at 75° C. and stirred for 0.5 hour, and then separated by using a separatory funnel. The dicarboxylic acid content in the wastewater obtained through the separation was lower than 0.2%, and the extraction yield of the organic phase was greater than 98%. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 6

500 ml of a hexadecanedioic acid fermentation broth after the termination of fermentation according to the method described in Example 8 of Patent ZL200410018255.7 was taken, in which the dicarboxylic acid content was 106.2 g/L. To the hexadecanedioic acid fermentation broth, 20 ml of 98% concentrated sulfuric acid was added, and then a mixture of about 400 g butyl acetate and 400 g n-butanol was added. The solution was maintained in a water bath at 80° C. and stirred for 20 minutes, and then separated by using a separatory funnel. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 7

600 ml of a dodecanedioic acid fermentation broth after the termination of fermentation according to the method described in Example 12 of Patent ZL200410018255.7 was taken, in which the dicarboxylic acid content was 47.7 g/L. To the dodecanedioic acid fermentation broth, about 300 g of butyl acetate was added, and 17 ml of 98% concentrated sulfuric acid was added. The solution was then maintained in a water bath at 85° C. and stirred for 1 hour, and then separated by using a separatory funnel. The dicarboxylic acid content in the wastewater obtained through the separation was lower than 0.2%, and the extraction yield of the organic phase was greater than 98%. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 8

500 ml of a dodecanedioic acid fermentation broth after the termination of fermentation according to the method described in Example 4 of Patent ZL200410018255.7 was taken, in which the dicarboxylic acid content was 168 g/L. To the dodecanedioic acid fermentation broth, 40 ml of 98% concentrated sulfuric acid was added, and then about 800 g of perchloroethylene was added. The solution was maintained in a water bath at 80° C. and stirred for 40 minutes, and then separated by using a separatory funnel. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 9

500 ml of a dodecanedioic acid fermentation broth after the termination of fermentation in Example 4 of Patent ZL200410018255.7 was taken, in which the dicarboxylic acid content was 168 g/L. To the dodecanedioic acid fermentation broth, 40 ml of 98% concentrated sulfuric acid was added, and then about 900 g of perchloroethylene was added. The solution was maintained in a water bath at 80° C. and stirred for 50 minutes, and then separated by using a separatory funnel. The organic phase obtained through the separation was cooled to room temperature and filtered, to obtain the dicarboxylic acid product. The resulting product was detected for the dicarboxylic acid content, the ash content, the nitrogen content and the transmittance, with the results seen in Table 1.

Example 10

600 ml of a dodecanedioic acid fermentation broth after the termination of fermentation according to the method described in Example 4 of Patent ZL200410018255.7 was taken, in which the dicarboxylic acid content was 195 g/L. To the dodecanedioic acid fermentation broth, 20 ml of 98% concentrated sulfuric acid was added, and then about 1,600 g of butyl acetate was added. The solution was maintained in a water bath at 30° C. and stirred for 10 minutes, and then separated by using a separatory funnel. The organic phase obtained through the separation was concentrated to 360 g through evaporation, and filtered at 60° C. when being hot, to obtain the product. The resulting product was detected for the dicarboxylic acid content, the ash content, the nitrogen content and the transmittance, with the results seen in Table 1.

TABLE 1

The quality of the products in the comparative example and the examples

| Examples | Dicarboxylic acid content (%) | Ash content (ppm) | Total nitrogen (ppm) | Transmittance (430 nm) |
|---|---|---|---|---|
| Comparative Example 1 | 97.5% | 2000 | 560 | 35 |
| Example 1 | 99.5% | 40 | 41 | 88 |
| Example 2 | 98.0% | 20 | 15 | 82 |
| Example 3 | 99.2% | 87 | 110 | 75 |
| Example 4 | 99.3% | 42 | 60 | 78 |
| Example 5 | 99.1% | 46 | 74 | 72 |
| Example 6 | 98.0% | 89 | 78 | 77 |
| Example 7 | 99.4% | 41 | 58 | 80 |
| Example 8 | 98.3% | 96 | 102 | 72 |
| Example 9 | 99.1% | 47 | 63 | 84 |
| Example 10 | 99.8% | 30 | 20 | 94 |

It can be known from the comparison of Examples 1 to 10 and the comparative Example 1 of the present invention above that, the process of the present invention can realize effective treatment of the fermentation broth containing a long chain dicarboxylic acid in a shorter period of time, the production efficiency is high, the yield of the product is high, and the product quality is good.

Herein, the yield refers to the content percent of the amount of the long chain dicarboxylic acid in the phase rich in the long chain dicarboxylic acid relative to the amount of the long chain dicarboxylic acid contained in the reaction solution.

For the long chain dicarboxylic acid product obtained by adopting the present invention, significant improvements in both the color and the impurity content are achieved, compared with the prior extraction processes. Due to the requirements for the quality of the long chain dicarboxylic acid product of downstream customers, the product obtained by the prior extraction process must be further purified, so as to meet the requirements of downstream applications such as production of perfumes and polymers and the like. By adopting the production process of the present invention, a high-quality product can be obtained in one step, and the product performance can meet the requirements of the most downstream customers for the long chain dicarboxylic acid.

Although merely the fermentation broth, the clear solution from the fermentation broth after passing through a ceramic membrane, and the clear solution of the fermentation broth after centrifugation are used to illustrate the process of the present invention in the examples of the present invention, it can be understood by persons skilled in the art that the process of the present invention is not limited to the fermentation broth, the clear solution of the fermentation broth after passing through a ceramic membrane, and the clear solution of the fermentation broth after centrifugation, but can be equally used in other reaction solutions comprising a long chain dicarboxylate.

Optional embodiments of the present invention are described in the above, so as to teach persons skilled in the art how to implement and reproduce the present invention. In order to teach the technical solutions of the present invention, some routine aspects are simplified or omitted. After reading the specification of the present invention, persons skilled in the art can easily think of variations or alternatives of the technical solutions of the present invention for achieving the objectives of the present invention according to common knowledge in the chemical field, and persons skilled in the art should understand that variations or alternatives originating from these embodiments will fall within the scope of the present invention.

The invention claimed is:

1. A process for treating a fermentation broth reaction solution containing a long chain dicarboxylate, microbial cells and residual alkanes or fatty acids to isolate a substantially pure long chain dicarboxylic acid, characterized by comprising:
   acidifying the fermentation broth reaction solution to convert the long chain dicarboxylate into a long chain dicarboxylic acid,
   adding an extractant to the fermentation broth reaction solution containing the long chain dicarboxylic acid, wherein the extractant is selected from the group consisting of $C_2$-$C_8$ alcohols esters of formic acid or acetic acid, $C_4$-$C_8$ alcohols, ethers, ketones, benzenes, and a mixture of two or more thereof,
   separating a phase rich in the long chain dicarboxylic acid from the fermentation broth reaction solution, and
   isolating the substantially pure long chain dicarboxylic acid from the separated phase, wherein the substantially pure long chain dicarboxylic acid comprises at least 98.5% long chain dicarboxylic acid, and
   wherein the extraction is performed at a temperature in the range from room temperature to the temperature below the boiling point of the phase rich in the long chain dicarboxylic acid and below 100° C.

2. The process according to claim 1, characterized in that, further comprising separating the long chain dicarboxylic acid is further separated by cooling the phase rich in the long chain dicarboxylic acid and separating a precipitated long chain dicarboxylic acid or by heating the phase rich in the long chain dicarboxylic acid to evaporate the extractant.

3. The process according to claim 1, characterized in that, the long chain dicarboxylic acid is a saturated or unsaturated straight chain dicarboxylic acid having 9 to 18 carbon atoms, with a carboxyl group at two ends of the chain.

4. The process according to claim 1, characterized in that, the long chain dicarboxylic acid is selected from the group consisting of nonanedioic acid, decanedioic acid, undecanedioic acid, dodecanedioic acid, tridecanedioic acid, tetradecanedioic acid, pentadecanedioic acid, hexadecanedioic acid, heptadecanedioic acid, octadecanedioic acid and 9-ene-octadecanedioic acid.

5. The process according to claim 1, characterized in that, the extractant is selected from the group consisting of n-butanol, isobutanol, n-pentanol, isopentanol, hexanol, cyclohexanol, 2-ethylhexanol, isooctanol, sec-octanol, toluene, xylene, ethylbenzene, methyl isobutyl ketone, butyl formate, propyl acetate, isoamyl acetate, isobutyl acetate, isopropyl acetate, n-amyl acetate, ethyl acetate, butyl acetate, octyl acetate, isooctyl acetate, sec-octylacetate, isopropyl ether, butyl ether, amyl ether and isoamyl and a mixture of two or more thereof.

6. The process according to claim 1, characterized in that, the acidification is performed by using an inorganic acid.

7. The process according to claim 1, characterized in that, the acidification is performed by using an acid selected from the group consisting of hydrochloric acid, sulfuric acid, phosphoric acid and nitric acid.

8. The process according to claim 1, characterized in that, the extraction is performed at a temperature in the range from 60° C. to the boiling point of the phase rich in the long chain dicarboxylic acid and below 100° C.

9. The process according to claim 1, characterized in that, the extractant is selected from the group consisting of propyl acetate, isoamyl acetate, isobutyl acetate, isopropyl acetate, n-amyl acetate, ethyl acetate, butyl acetate, octyl acetate, isooctyl acetate, sec-octylacetate, and a mixture of two or more thereof.

10. The process according to claim 1, characterized in that, the extractant is butyl acetate.

11. The process according to claim 1, characterized in that, the long chain dicarboxylic acid is a saturated straight chain dicarboxylic acid having 11 to 14 carbon atoms, with a carboxyl group at two ends of the chain.

12. The process according to claim 11, characterized in that, the saturated straight chain dicarboxylic acid has 12 carbon atoms.

13. The process according to claim 1, characterized in that, the substantially pure long chain dicarboxylic acid comprises at least about 98.5% long chain dicarboxylic acid.

* * * * *